United States Patent [19]
Kamihara et al.

[11] Patent Number: 5,461,157
[45] Date of Patent: Oct. 24, 1995

[54] PROCESS FOR PREPARING PYRROLIDINYLACETAMIDE DERIVATIVES

[75] Inventors: Shinji Kamihara; Tohru Kaneuchi; Keiji Uchiyama; Tatsuya Terada, all of Tokyo, Japan

[73] Assignee: Daiichi Pharmaceutical Co., Ltd., Tokyo, Japan

[21] Appl. No.: 356,503

[22] Filed: Dec. 15, 1994

Related U.S. Application Data

[63] Continuation-in-part of Ser. No. 77,916, Jun. 18, 1993, abandoned.

[30] Foreign Application Priority Data

Jun. 19, 1992 [JP] Japan ..................... 4-160496

[51] Int. Cl.$^6$ .................................... C07D 201/27
[52] U.S. Cl. .......................................... 548/550
[58] Field of Search ............................. 548/550

[56] References Cited

U.S. PATENT DOCUMENTS 5,059,687  10/1991  Schröder et al. ................ 548/546

OTHER PUBLICATIONS

Daskalov, Kh.; Georgiev, A.; Konstantinova, K.; (Bulgaria), Tr. Nauchnoizsled Khim.–Farm Inst., (1985). 15. p. 21–32 (and Abstract translated).

*Yakugaku Zasshi* (Pharmacological Journal), vol. 99(2), pp. 146–254 (1979).

*Primary Examiner*—David B. Springer
*Attorney, Agent, or Firm*—Sughrue, Mion, Zinn, Macpeak & Seas

[57] ABSTRACT

A process for preparing a 2-(1-pyrrolidinyl)acetamide derivative useful as a cerebral function improving agent is disclosed, comprising reacting a halogenoacetamide derivative with substituted or unsubstituted 2-pyrrolidinone, the halogenoacetamide derivative being prepared by reacting an amine and a halogenoacetyl chloride. High yields of the intermediate compound as well as the final product are attained at low cost.

13 Claims, No Drawings

PROCESS FOR PREPARING PYRROLIDINYLACETAMIDE DERIVATIVES

CROSS REFERENCE TO RELATED APPLICATION

This application is a continuation-in-part of U.S. Ser. No. 08/077,916 filed Jun. 18, 1993, now abandoned.

FIELD OF THE INVENTION

The present invention relates to a process for preparing a pyrrolidinylacetamide derivative useful as an agent for improving cerebral functions.

BACKGROUND OF THE INVENTION

Known processes for preparing pyrrolidinylacetamide derivatives include a process comprising reacting pyrrolidinylacetic acid or a reactive derivative thereof with an amine in an organic solvent in the presence of dicyclohexylcarbodiimide as disclosed in U.S. Pat. No. 4,341,790 and JP-A-56-2960 (the term "JP-A" as used herein means an "unexamined published Japanese patent application").

The above process is not suited for production on an industrial scale due to disadvantages, such as use of expensive dicyclohexylcarbodiimide as a condensing agent, involvement of complicated steps for separation and removal of dicyclohexylurea which is a by-product from dicyclohexylcarbodiimide, poor overall yield. Moreover, the starting material, e.g., 2-oxo-1-pyrrolidinylacetic acid, should be produced by reacting 2-pyrrolidinone with methyl bromoacetate and hydrolyzing the resulting methyl 2-oxo-1-pyrrolidinylacetate, and purified by distilling the reaction mixture under high pressure and at high temperature. These complicated operations and low yield are disadvantageous for industrial production.

On the other hand, a process for preparing N-substituted lactams is known as disclosed in British Patent No. 1,039,113. This known process comprises reacting an N-unsubstituted lactam with an alkali metal hydride and then reacting the resulting alkali metal derivative with an appropriate ω-chloroalkylamide. The chloroacetanilide derivative used in the process is prepared by a manner as disclosed, for example, in *Yakugaku Zasshi* (Pharmacological Journal), vol. 99(2), pp. 146 to 154 (1979), which comprises reacting xylidine with monochloroacetyl chloride in a glacial acetic acid to obtain 2,6-dimethylmonochloroacetanilide in a 78 to 80% yield. However, these processes are not still satisfactory from the viewpoint of yield on an industrial scale.

SUMMARY OF THE INVENTION

An object of the present invention is to provide a process for preparing a pyrrolidinylacetamide derivative which is free from the above-mentioned disadvantages associated with the known process and excellent from an economical standpoint.

The base of the present invention consists in a reaction of a halogenoacetamide derivative and 2-pyrrolidinone, with various improvements added thereto, for example, an improvement in which the starting halogenoacetamide derivative is obtained in a high yield by reacting an amine and a halogenoacetyl chloride in a two-phase reaction system.

The present invention provides a process for preparing a 2-(1-pyrrolidinyl)acetamide derivative represented by formula (I):

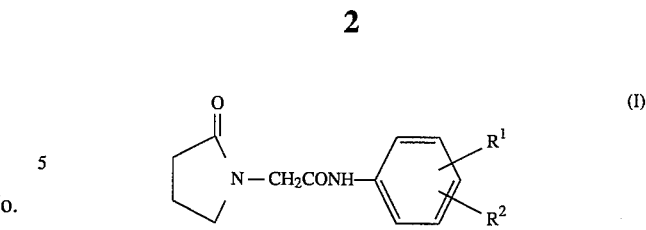

wherein $R^1$ and $R^2$ represent independently a hydrogen atom or an alkyl group having from 1 to 5 carbon atoms, comprising reacting an amine represented by formula (III):

wherein $R^1$ and $R^2$ are as defined above, with a halogenoacetyl chloride, wherein the halogenoacetyl is chloroacetyl or bromoacetyl, at a temperature less than 50° C. in a two-phase reaction system composed of a basic aqueous layer and an organic solvent layer, to obtain a halogenoacetamide derivative represented by formula (II):

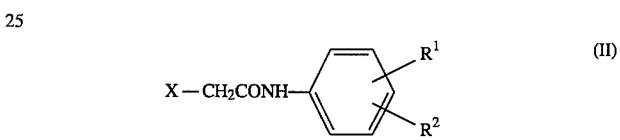

wherein $R^1$ and $R^2$ are defined above; and X represents a chlorine atom or a bromine atom, and reacting the resulting halogenoacetamide derivative of formula (II) with a metal salt of 2-pyrrolidinone.

DETAILED DESCRIPTION OF THE INVENTION

The 2-(1-pyrrolidinyl)acetamide derivative of formula (I) is a known compound disclosed in U.S. Pat. No. 4,341,790 and JP-A-56-2960. Of the compounds of formula (I), the most useful is N-(2,6-dimethylphenyl)-2-(2-oxo-1-pyrrolidinyl)acetamide.

The process of the present invention for preparing the 2-(1-pyrrolidinyl)acetamide derivative of formula (I) is illustrated by the following reaction equations.

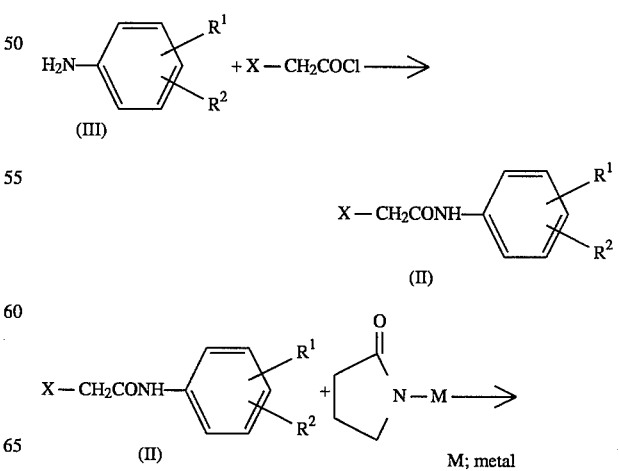

-continued

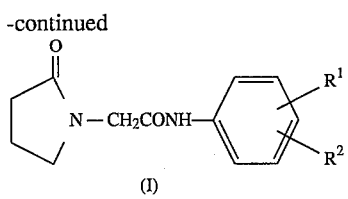

(I)

Each reaction is described hereinafter in detail.

An amine (III) and a halogenoacetyl chloride are reacted in a two phase system. The two phase system consists of an aqueous layer and an organic solvent layer.

Suitable organic solvents in this system are those being inert to the starting materials, such as chloroform, methylene chloride, dichloroethylene, toluene, xylene, ethyl acetate, t-butyl methyl ether, acetone, and acetonitrile. Toluene and xylene are particularly suitable from the viewpoint of recovery and reduction of pollution caused by the halogen compound as well as the reaction yield.

The aqueous layer should be basic for satisfactory progress of the reaction. A base, such as sodium carbonate, sodium hydrogencarbonate, sodium hydroxide, potassium hydroxide, etc., is preferably added in at least an equivalent amount.

The halogenoacetyl chloride which can be used in the present invention is preferably chloroacetyl chloride, which gives a chloroacetamide derivative of formula (II).

The molar ratio of the halogenoacetyl chloride to the amine is at least 1.0, and preferably 1.1 to about 1.5.

It is preferable to stir the two phase mixture to accelerate the reaction. The mixture is allowed to react at a temperature below 50° C., and preferably from 15 to 40° C., to obtain the product in a high yield, since the reaction at high temperatures produces impurities. More preferably, the reaction is carried out at a temperature of from 20° to 35° C.

The reaction product (II) can be isolated in a usual manner, for example, (1) by cooling the reaction mixture and collecting the resulting precipitate by filtration, or (2) by separating and concentrating the organic layer and collecting the resulting precipitate by filtration.

Though the intermediate of formula (II) can be isolated as described above, it is advantageous for industrial purposes to use the separated organic layer in the subsequent step without isolating such intermediate. Since few by-products are produced in this reaction, it is not necessary to conduct complicated steps for purification. Practically, the organic layer separated is azeotropically distilled under reduced pressure to about ½ to ⅓ by volume, thus the water content in the organic solvent comes within an allowable limit (about 0.05% v/v).

The resulting halogenoacetamide derivative (II) is then reacted with a metal salt of 2-pyrrolidinone to produce pyrrolidinylacetamide derivative.

The metal salt of 2-pyrrolidinone is formed by treating 2-pyrrolidinone with a metal compound which functions as a proton accepter, such as potassium hydride, sodium hydride, sodium amide, n-butyl lithium, t-butyl lithium, diethylamino lithium and alkali metal alcoholares. Of these metal compounds, it is preferred to use various alcoholates which are less expensive and less ignitable and to carry out the treatment under heating at about 100° to 150° C. for 0.5 to 5 hours while removing the by-produced alcohol from the system. In particular, sodium methylate and sodium ethylate are preferred because of cheapness and easy removal of the by-produced methanol or ethanol. The amount of metal compound to be used is preferably not more than an equimolar amount with the pyrrotidinone. Use of the metal compound in excess tends to cause side reactions.

The treatment with a metal compound is usually carried out in an appropriate solvent which is unreactive with the metal compound. Examples of suitable solvents include toluene, xylene, and t-butyl methyl ether. The treatment is preferably conducted in a water-free system, such as in a nitrogen stream, because water, if present, may react with the metal compound or may interfere with the reaction.

To the mixture obtained by the above-mentioned treatment with a metal compound is added the halogenoacetamide derivative (II) or organic layer containing thereof.

The halogenoacetamide derivative (II) is usually used in an amount not more than an equimolar amount with the resulting metal salt of 2-pyrrolidinone in the abovementioned treatment.

The mixture is allowed to react at a temperature of from 0° to 100° C., and preferably from 40° to 80° C., to obtain the desired pyrrolidinylacetamide derivative (I).

The reaction product can easily be isolated by cooling the reaction mixture to precipitate. In the industrial process, it is convenient to add hot water of about 70° to 85° C. to the reaction mixture and allow it to cool. The desired product may be precipitated in the water layer and be collected by filtration.

The present invention will now be illustrated in greater detail with reference to Examples, but it should be understood that the present invention is not construed as being limited thereto.

EXAMPLE 1

Preparation of
2-Chloro-N-(2,6-dimethylphenyl)acetamide

In 3 l of toluene was dissolved 182 g of 2,6-xylidine, and in 1.5 l of water was dissolved 159 g of sodium carbonate. The two solutions were combined, and 203 g of chloroacetyl chloride was added thereto dropwise over 1.5 hours at an inner temperature of from 20° to 35° C., followed by stirring at that temperature for 1.5 hours. The reaction mixture was cooled with ice, and the precipitated crystals were collected by filtration and dried under reduced pressure to obtain 282 g (95%) of the titled compound.

Melting point: 148°–148.5° C.

$^1$H-NMR (CDCl$_3$): 2.24 (6H, s), 4.24 (2H, s), 7.16 (3H, s), 7.9 (1H, br s)

EXAMPLE 2

Preparation of
2-Chloro-N-(2,6-dimethylphenyl)acetamide

In 4 l of 1,2-dichloroethylene was dissolved 182 g of 2,6-xylidine, and 1.6 l of a 1N sodium hydroxide aqueous solution was added thereto, followed by stirring. To the mixture was added dropwise 203 g of chloroacetyl chloride over 1.5 hours at an inner temperature between 20 and 35° C. The mixture was stirred at that temperature for 1.5 hours. The reaction mixture was separated into two layers, and the organic layer was concentrated under reduced pressure. The precipitate was collected by filtration and dried under reduced pressure to obtain 282 g (95%) of the titled compound.

Melting point: 148°–148.5° C.

¹H-NMR data agreed with those of Example 1.

EXAMPLE 3

Preparation of N-(2,6-Dimethylphenyl)-2-(2-oxo-1-pyrrolidinyl)acetamide

In 300 ml of toluene was suspended 9.2 g of 60% sodium hydride in a nitrogen stream, and 21.3 g of 2pyrrolidinone was slowly added dropwise to the suspension at an inner temperature controlled at 40° C. or lower. After stirring the mixture for 2 hours, 19.7 g of 2-chloro-N(2,6-dimethylphenyl)acetamide was added thereto, and the mixture was allowed to react at 60° to 70° C. for 2 hours. To the reaction mixture was added 50 ml of hot water of about 70° to 85° C., followed by allowing to cool with stirring. The precipitated crystals in the aqueous layer were collected by filtration and dried under reduced pressure to obtain 22.2 g (90%) of the titled compound.

Melting point: 153°–153.5° C.

¹H-NMR (CDCl₃): 1.9–2.6 (4H, m), 2.18 (6H, s), 3.57 (2H, t, J=6.8Hz), 4.07 (2H, s), 7.06 (3H, s), 7.9 (1H, br s)

EXAMPLE 4

Preparation of N-(2,6-Dimethylphenyl)-2-(2-oxo-1-pyrrolidinyl]acetamide

In 30 ml of t-butyl methyl ether was suspended 897 mg of sodium amide in a nitrogen stream, and 2.13 g of 2-pyrrolidinone was slowly added thereto dropwise, followed by refluxing for 2 hours. After allowing to cool, 1.97 g of 2-chloro-N-(2,6-dimethylphenyl)acetamide was added thereto, followed by refluxing for 2 hours. To the reaction mixture was added 50 ml of hot water of about 70° to 85° C., and the mixture was allowed to cool with stirring. The thus formed crystals in the aqueous layer were collected by filtration and dried under reduced pressure to obtain 2.19 g (89%) of the titled compound.

Melting point: 151°–152.5° C.

EXAMPLE 5

Preparation of N-(2,6-Dimethylphenyl)-2-(2-oxo-1-pyrrolidinyl)acetamide

In 300 ml of toluene was suspended 9.0 g of sodium amide in a nitrogen stream, and 21.3 g of 2-pyrrolidinone was slowly added thereto dropwise. After stirring the mixture at 60° to 70° C. for 2 hours, 19.7 g of 2-chloro-N-(2,6-dimethylphenyl)acetamide was added thereto, followed by allowing to react at 60° to 70° C. for 2 hours. To the reaction mixture was added 50 ml of hot water of about 70° to 85° C., and the mixture was allowed to cool with stirring. The precipitated crystals in the aqueous layer were recovered by filtration and dried under reduced pressure to obtain 22.4 g (91%) of the titled compound.

Melting point: 152°–152.5° C.

EXAMPLE 6

Preparation of N-(2,6-Dimethylphenyl)-2-(2-oxo-1-pyrrolidinyl)acetamide

In 5 l of toluene was suspended 203 g of sodium methylate, and 511 g of 2-pyrrolidinone was added thereto. The mixture was slowly heated up to 100° to 110° C., at which it was allowed to react for 3 hours. During the reaction, about 300 ml of toluene was distilled off. After allowing to cool, 296 g of 2-chloro-N-(2,6-dimethylphenyl)acetamide was added thereto to react at 60° to 70° C. for 2 hours. To the reaction mixture was added 300 ml of hot water of about 70° to 85° C., followed by allowing to cool with stirring. The crystals formed in the aqueous layer were collected by filtration and dried under reduced pressure to obtain 332 g (90%) of the titled compound.

Melting point: 152.5°–153° C.

EXAMPLE 7

Preparation of N-(2,6-Dimethylphenyl)-2-(2-oxo-1-pyrrolidinyl)acetamide

In 5 l of toluene was dissolved 182 g of 2,6-xylidine, and in 1.5 l of water was dissolved 159 g of sodium carbonate. The two solutions were combined, and 203 g of chloroacetyl chloride was added thereto dropwise over 1.5 hours at an inner temperature of from 20° to 35° C., followed by stirring at that temperature for 1.5 hours. The reaction mixture was heated to about 70° C. to dissolve the precipitated crystals and then separated into two layers. The organic layer was concentrated under reduced pressure to about 500 ml. The resulting suspension of 2-chloro-N-(2,6-dimethylphenyl)acetamide was allowed to cool.

Separately, 203 g of sodium methylate was suspended in 4 l of toluene, and 511 g of 2-pyrrolidinone was added thereto. The mixture was slowly heated up to 100° to 110° C., at which it was allowed to react for 3 hours. During the reaction, about 300 ml of toluene was distilled off. After allowing to cool, the above prepared suspension of 2-chloro-N-(2,6-dimethylphenyl)acetamide was added thereto to react at 60° to 70° C. for 2 hours. To the reaction mixture was added 300 ml of hot water of about 70° to 85° C., followed by allowing to cool with stirring. The crystals formed in the aqueous layer were collected by filtration and dried under reduced pressure to obtain 336 g (91%) of the titled compound.

Melting point: 152°–153° C.

While the invention has been described in detail and with reference to specific examples thereof, it will be apparent to one skilled in the art that various changes and modifications can be made therein without departing from the spirit and scope thereof.

What is claimed is:

1. A process for preparing a 2-(1-pyrrolidinyl)acetamide derivative represented by formula (I):

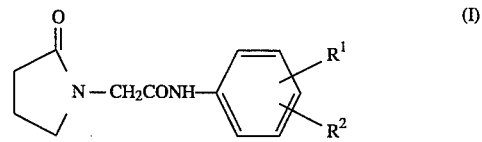

wherein R¹ and R² represent independently a hydrogen atom or an alkyl group having from 1 to 5 carbon atoms, comprising reacting 2-pyrrolidinone with an alkali metal alcoholate, and reacting the resulting metal salt of 2-pyrrolidinone with a halogenoacetamide derivative represented by formula II:

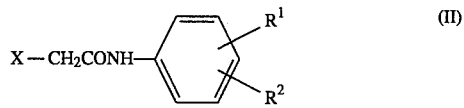

wherein R¹ and R² are as defined above; and X represents a chlorine atom or a bromine atom.

2. A process for preparing a halogenoacetamide derivative represented by formula (II):

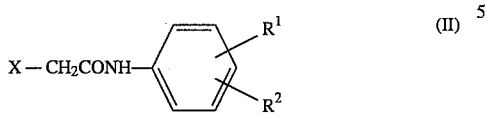

wherein $R^1$ and $R^2$ represent independently a hydrogen atom or an alkyl group having from 1 to 5 carbon atoms; and X represents a chlorine atom or a bromine atom, comprising reacting an amine represented by formula (III):

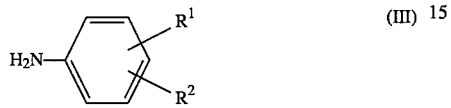

wherein $R^1$ and $R^2$ are as defined above, with a halogenoacetyl chloride, wherein the halogenoacetyl is chloroacetyl or bromoacetyl, at a temperature less than 50° C. in a two-phase reaction system composed of a basic aqueous layer and an organic solvent layer.

3. A process for preparing a 2-(1-pyrrolidinyl)acetamide derivative represented by formula (I):

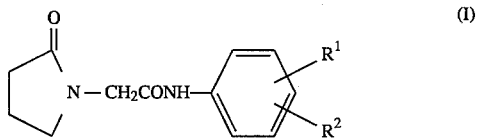

wherein $R^1$ and $R^2$ represent independently a hydrogen atom or an alkyl group having from 1 to 5 carbon atoms, comprising reacting an amine represented by formula (III):

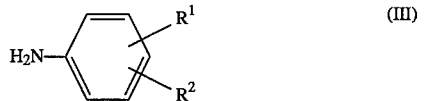

wherein $R^1$ and $R^2$ are as defined above, with a halogenoacetyl chloride, wherein the halogenoacetyl is chloroacetyl or bromoacetyl, at a temperature less than 50° C. in a two-phase reaction system composed of a basic aqueous layer and an organic solvent layer, to obtain a halogenoacetamide derivative represented by formula (II):

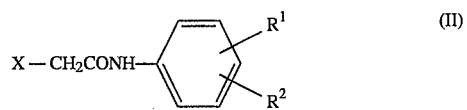

wherein $R^1$ and $R^2$ are as defined above; and X represents a chlorine atom or a bromine atom, and reacting the resulting halogenoacetamide derivative of formula (II) with a metal salt of 2-pyrrolidinone wherein the metal salt of 2-pyrrolidinone was prepared by reacting 2-pyrrolidinone with an alkali metal alcoholate.

4. A process as claimed in claim 1, wherein X is a chlorine atom.

5. A process as claimed in claim 1, wherein said halogenoacetamide derivative is 2-chloro-N-(2,6-dimethylphenyl)acetamide.

6. A process as claimed in claim 1, wherein said halogenoacetamide derivative is 2-chloro-N-(2,6-dimethylphenyl)acetamide, and said alkaline metal alcoholate is sodium methylate or sodium ethylate.

7. A process as claimed in claim 2, wherein said halogenoacetyl chloride is chloroacetyl chloride, and said halogenoacetamide derivative is a chloroacetamide derivative.

8. A process as claimed in claim 3, wherein said halogenoacetyl chloride is chloroacetyl chloride, and said halogenoacetamide derivative is a chloroacetamide derivative.

9. A process as claimed in claim 2, wherein said halogenoacetyl chloride is chloroacetyl chloride, and said amine is 2,6-xylidine.

10. A process as claimed in claim 3, wherein said halogenoacetyl chloride is chloroacetyl chloride, and said amine is 2,6-xylidine.

11. A process as claimed in claim 2, wherein said halogenoacetyl chloride is chloroacetyl chloride, said amine is 2,6-xylidine and said organic solvent is toluene or xylene.

12. A process as claimed in claim 3, wherein said halogenoacetyl chloride is chloroacetyl chloride, said amine is 2,6-xylidine and said alkali metal alcoholate is sodium methylate or sodium ethylate.

13. A process as claimed in claim 3, wherein said halogenoacetyl chloride is chloroacetyl chloride, said amine is 2,6-xylidine, said alkali metal alcoholate is sodium methylate or sodium ethylate and said organic solvent is toluene or xylene.

* * * * *